US00PP30364P2

(12) United States Plant Patent
Pieters

(10) Patent No.: US PP30,364 P2
(45) Date of Patent: Apr. 9, 2019

(54) ***CHRYSANTHEMUM* PLANT NAMED 'LANO PURPLE'**

(50) Latin Name: ***Chrysanthemum* X *morifolium***
Varietal Denomination: LANO PURPLE

(71) Applicant: Elien Sofie Pieters, Oostnieuwkerke (BE)

(72) Inventor: Elien Sofie Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 0 days.

(21) Appl. No.: 15/732,908

(22) Filed: Jan. 13, 2018

(51) Int. Cl.
*A01H 5/02* (2018.01)

(52) U.S. Cl.
USPC ..... Plt./287
CPC ..... *A01H 5/02* (2013.01)

(58) Field of Classification Search
USPC ..... Plt./287
CPC ..... A01H 5/0255
See application file for complete search history.

*Primary Examiner* — Kent L Bell
(74) *Attorney, Agent, or Firm* — C. A. Whealy

(57) ABSTRACT

A new and distinct cultivar of *Chrysanthemum* plant named 'LANO PURPLE', characterized by its upright, outwardly spreading and uniformly rounded plant habit; moderately vigorous growth habit; freely branching habit; dense and full plant habit; dark green-colored leaves; uniform and freely flowering habit; long flowering period; and decorative-type inflorescences with purple-colored ray florets.

1 Drawing Sheet

Botanical designation: *Chrysanthemum* X *morifolium*.
Cultivar denomination: 'LANO PURPLE'.

BACKGROUND OF THE INVENTION

The present invention relates to a new and distinct cultivar of *Chrysanthemum* plant, botanically known as *Chrysanthemum* X *morifolium* and hereinafter referred to by the name 'LANO PURPLE'.

The new *Chrysanthemum* plant is a product of a planned breeding program conducted by the Inventor in Oostnieuwkerke, Belgium. The objective of the breeding program is to create new uniformly mounding and freely flowering *Chrysanthemum* plants with unique and attractive ray floret coloration.

The new *Chrysanthemum* plant originated from a cross-pollination made by the Inventor in October, 2012 in Oostnieuwkerke, Belgium of *Chrysanthemum* X *morifolium* 'Five Alarm Red', not patented, as the female, or seed, parent with *Chrysanthemum* X *morifolium* 'Pomax Purple', not patented, as the male, or pollen, parent. The new *Chrysanthemum* plant was discovered and selected by the Inventor as a single flowering plant from within the progeny of the stated cross-pollination in a controlled greenhouse environment in Oostnieuwkerke, Belgium in October, 2013.

Asexual reproduction of the new *Chrysanthemum* plant by vegetative terminal cuttings was first conducted in a controlled greenhouse environment in Oostnieuwkerke, Belgium in January, 2014. Asexual reproduction by vegetative terminal cuttings has shown that the unique features of this new *Chrysanthemum* plant are stable and reproduced true to type in successive generations.

SUMMARY OF THE INVENTION

The following traits have been repeatedly observed and are determined to be the unique characteristics of 'LANO PURPLE'. These characteristics in combination distinguish 'LANO PURPLE' as a new and distinct *Chrysanthemum* plant:

1. Upright, outwardly spreading and uniformly rounded plant habit; moderately vigorous growth habit.
2. Freely branching habit; dense and full plant habit.
3. Dark green-colored leaves.
4. Uniform and freely flowering habit.
5. Long flowering period.
6. Decorative-type inflorescences with purple-colored ray florets.

Plants of the new *Chrysanthemum* can be compared to plants of the female parent, 'Five Alarm Red'. Plants of the new *Chrysanthemum* differ primarily from plants of 'Five Alarm Red' in the following characteristics:

1. Plants of the new *Chrysanthemum* are more uniform than plants of 'Five Alarm Red'.
2. Plants of the new *Chrysanthemum* are more flexible than plants of 'Five Alarm Red'.
3. Inflorescences of plants of the new *Chrysanthemum* are smaller than inflorescences of plants of 'Five Alarm Red'.
4. Ray florets of plants of the new *Chrysanthemum* are purple in color whereas ray florets of plants of 'Five Alarm Red' are dark red in color.

Plants of the new *Chrysanthemum* can be compared to plants of the male parent, 'Pomax Purple'. Plants of the new *Chrysanthemum* differ primarily from plants of 'Pomax Purple' in the following characteristics:

1. Plants of the new *Chrysanthemum* are not as vigorous as plants of 'Pomax Purple'.
2. Plants of the new *Chrysanthemum* flower about three weeks earlier than plants of 'Pomax Purple'.

Plants of the new *Chrysanthemum* can be compared to plants of the *Chrysanthemum* X *morifolium* 'Zaza Purple', disclosed in U.S. Plant patent application Ser. No. 15/731, 853. In side-by-side comparisons, plants of the new *Chrysanthemum* differ primarily from plants of 'Zaza Purple' in the following characteristics:

1. Plants of the new *Chrysanthemum* are not as flexible as plants of 'Zaza Purple'.
2. Plants of the new *Chrysanthemum* flower more uniformly and later than plants of 'Zaza Purple'.
3. Inflorescences of plants of the new *Chrysanthemum* are slightly smaller than inflorescences of plants of 'Zaza Purple'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type.

The photograph comprises a side perspective view of a typical flowering plant of 'LANO PURPLE' grown in a container.

DETAILED BOTANICAL DESCRIPTION

The aforementioned photograph and following observations and measurements describe plants grown in 19-cm containers in an outdoor nursery in Oostnieuwkerke, Belgium during the summer and autumn and under cultural practices generally used in commercial *Chrysanthemum* production. During the production of the plants, day temperatures ranged from 20° C. to 25° C. and night temperatures ranged from 12° C. to 18° C. Plants were 20 weeks old when the photograph and detailed description were taken. In the following description, color references are made to The Royal Horticultural Society Colour Chart, 2005 Edition, except where general terms of ordinary dictionary significance are used.

Botanical classification: *Chrysanthemum* X *morifolium* 'LANO PURPLE'.

Parentage:

*Female, or seed, parent.*—*Chrysanthemum* X *morifolium* 'Five Alarm Red', not patented.

*Male, or pollen, parent.*—*Chrysanthemum* X *morifolium* 'Pomax Purple', not patented.

Propagation:

*Type cutting.*—By vegetative tip cuttings.

*Time to initiate roots, summer.*—About two weeks at temperatures about 20° C.

*Time to initiate roots, winter.*—About 20 days at temperatures about 20° C.

*Time to produce a rooted young plant, summer.*—About 30 days at temperatures about 20° C.

*Time to produce a rooted young plant, winter.*—About 40 days at temperatures about 20° C.

*Root description.*—Fine, fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Appearance.*—Perennial decorative-type *Chrysanthemum*; stems upright and outwardly spreading giving a uniformly rounded appearance to the plant; plants roughly spherical; very freely branching habit, about 25 primary lateral branches develop, each primary lateral branch with multiple secondary branches; pinching enhances lateral branch development; dense and full plant habit; moderately vigorous growth habit; plants flexible, not brittle.

*Plant height.*—About 35 cm.

*Plant width.*—About 50 cm.

*Lateral branches.*—Length: About 25 cm. Diameter: About 2 mm to 3 mm. Internode length: About 2 cm. Strength: Strong, flexible. Texture: Pubescent, fine; longitudinally ridged. Color: Close to 136A.

*Leaves.*—Arrangement: Alternate, simple. Length: About 3.5 cm to 6 cm. Width: About 2.5 cm to 4 cm. Apex: Rounded to cuspidate. Base: Attenuate. Margin: Palmately lobed and serrate, sinuses between lateral lobes divergent to parallel. Texture, upper and lower surfaces: Slightly pubescent. Venation: Palmately reticulate. Color: Developing leaves, upper surface: Close to 137A. Developing leaves, lower surface: Close to 137C. Fully expanded leaves, upper surface: Close to 136A; venation, close to 148C. Fully expanded leaves, lower surface: Close to 137A; venation, close to 147B to 147C. Petioles: Length: About 1 cm. Diameter: About 2 mm. Texture, upper and lower surfaces: Slightly pubescent; rough. Color, upper surface: Close to 146C. Color, lower surface: Close to 146D. Stipules: Length: About 1 cm. Diameter: About 2 mm. Texture, upper and lower surfaces: Slightly pubescent; rough. Color, upper and lower surfaces: Close to 137A.

Inflorescence description:

*Appearance.*—Decorative-type inflorescence form; inflorescences borne on terminals above foliar plane; disc and ray florets arranged acropetally on a capitulum.

*Fragrance.*—Slightly fragrant, pungent.

*Flowering response.*—Under natural season conditions, plants flower in mid-September in Belgium; flowering response time, about 35 days.

*Postproduction longevity.*—Inflorescences maintain good color and substance for about 42 days in an outdoor nursery; inflorescences persistent.

*Quantity of inflorescences.*—About 30 inflorescences develop per lateral branch.

*Inflorescence buds.*—Height: About 6 mm. Diameter: About 1 cm. Shape: Globular. Color: Close to 136A.

*Inflorescence diameter.*—About 3.5 cm.

*Inflorescence depth (height).*—About 2 cm.

*Disc diameter.*—About 5 mm; inconspicuous.

*Receptacle diameter.*—About 3 mm.

*Receptacle height.*—About 2.5 mm to 3 mm.

*Receptacle color.*—Close to 144B.

*Ray florets.*—Length: About 3 cm to 4 cm. Width: About 4 mm. Shape: Oval. Apex: Rounded. Base: Attenuate. Margin: Entire. Aspect: Mostly flat. Texture and luster, upper and lower surfaces: Smooth, glabrous; matte. Number of ray florets per inflorescence: About 150 arranged in about ten whorls. Color: When opening, upper surface: Close to 83A. When opening, lower surface: Close to N81B. Fully opened, upper surface: Close to 77A; color becoming closer to 77B with development. Fully opened, lower surface: Close to 77B; color becoming closer to N80D with development.

*Disc florets.*—Length: About 3 mm. Diameter: About 0.5 mm to 1 mm. Shape: Tubular; apices acute. Number of disc florets per inflorescence: About 30 massed at the center of the inflorescence. Texture: Smooth, glabrous. Color, immature: Close to 145A. Color, mature: Close to 12A.

*Phyllaries*.—Number of phyllaries per inflorescence: About 25 arranged in two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Color, upper surface: Close to 137A. Color, lower surface: Close to N137B.

*Peduncles*.—Length, terminal peduncle: About 5 cm. Length, fourth peduncle: About 5 cm. Length, seventh peduncle: About 5 cm. Diameter: About 2 mm. Angle: About 30° from vertical. Strength: Moderately strong. Texture: Slightly pubescent. Color: Close to 136A.

*Reproductive organs*.—Androecium: Not observed. Gynoecium: Not observed.

*Seeds and fruits*.—To date seed and fruit production have not been observed on plants of the new *Chrysanthemum*.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'LANO PURPLE' as illustrated and described.

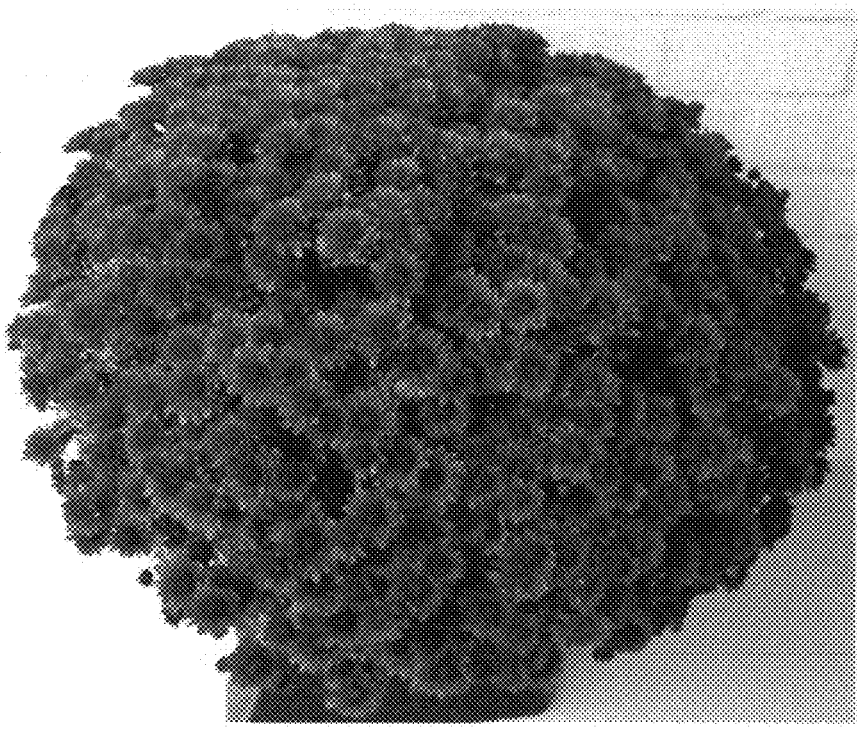

* * * * *